United States Patent [19]
Dahl et al.

[11] Patent Number: 5,300,106
[45] Date of Patent: Apr. 5, 1994

[54] INSERTION AND TUNNELING TOOL FOR A SUBCUTANEOUS WIRE PATCH ELECTRODE

[75] Inventors: Roger W. Dahl, Andover; James D. Kadera, St. Paul; Robert W. Wickham, Harris; J. Michael Hoch, Plymouth; John Heil, St. Paul, all of Minn.

[73] Assignee: Cardiac Pacemakers, Inc., St. Paul, Minn.

[21] Appl. No.: 710,716

[22] Filed: Jun. 7, 1991

[51] Int. Cl.$^5$ ............................................... A61N 1/05
[52] U.S. Cl. .................................... 607/119; 604/165
[58] Field of Search ................ 128/785, 786; 604/164, 604/160, 165

[56] References Cited

U.S. PATENT DOCUMENTS

| | | | |
|---|---|---|---|
| Re. 31,885 | 3/1985 | Osborne | 604/161 |
| 3,474,791 | 10/1969 | Bentov | 128/785 |
| 4,166,469 | 9/1979 | Littleford | 604/164 |
| 4,270,549 | 6/1981 | Heilman et al. | 128/784 |
| 4,393,883 | 7/1983 | Smyth et al. | 128/785 |
| 4,412,832 | 11/1983 | Kling et al. | 604/164 |
| 4,516,584 | 5/1985 | Garcia | 128/785 |
| 4,581,025 | 4/1986 | Timmermans | 604/160 |
| 4,596,559 | 6/1986 | Fleischhacker | 604/170 |
| 4,888,000 | 12/1989 | McQuilkin et al. | 604/164 |
| 5,005,587 | 4/1991 | Scott | 128/786 |
| 5,064,414 | 11/1991 | Revane | 604/165 |
| 5,104,388 | 4/1992 | Quackenbush | 604/164 |

FOREIGN PATENT DOCUMENTS

| | | |
|---|---|---|
| 0280528 | 8/1988 | European Pat. Off. . |
| 0362462 | 4/1990 | European Pat. Off. . |
| 2929233 | 1/1980 | Fed. Rep. of Germany . |
| 2103936 | 3/1983 | United Kingdom . |

*Primary Examiner*—William E. Kamm
*Assistant Examiner*—Scott M. Getzow
*Attorney, Agent, or Firm*—Keck, Mahin & Cate

[57] ABSTRACT

A tool for subcutaneously implanting a subcutaneous electrode comprising several wire patch electrode segments by way of a single surgical incision. The tunneling tool comprises a stylet and a peel-away sheath. The tunneling tool is inserted into an incision, in a direction which corresponds to the desired placement of an electrode segment. Once the tunneling tool reaches a desired position, the stylet is withdrawn, thereby revealing the interior of the peel-away sheath and a resulting subcutaneous tunnel. The corresponding electrode segment is then inserted into this subcutaneous tunnel, and subsequently implanted in the patient. The implantation procedure is then repeated as many times as is necessary, using the same incision, until all the electrode segments for the particular electrode configuration have been implanted. In addition, the tunneling tool can be adapted to conform to varying electrode segment sizes, which thereby allows the tool to conform to the varying needs of each individual patient. As an even further feature, the tunneling tool can be constructed in a curved configuration to facilitate electrode implantation in the lateral thoracic region of the body.

31 Claims, 6 Drawing Sheets

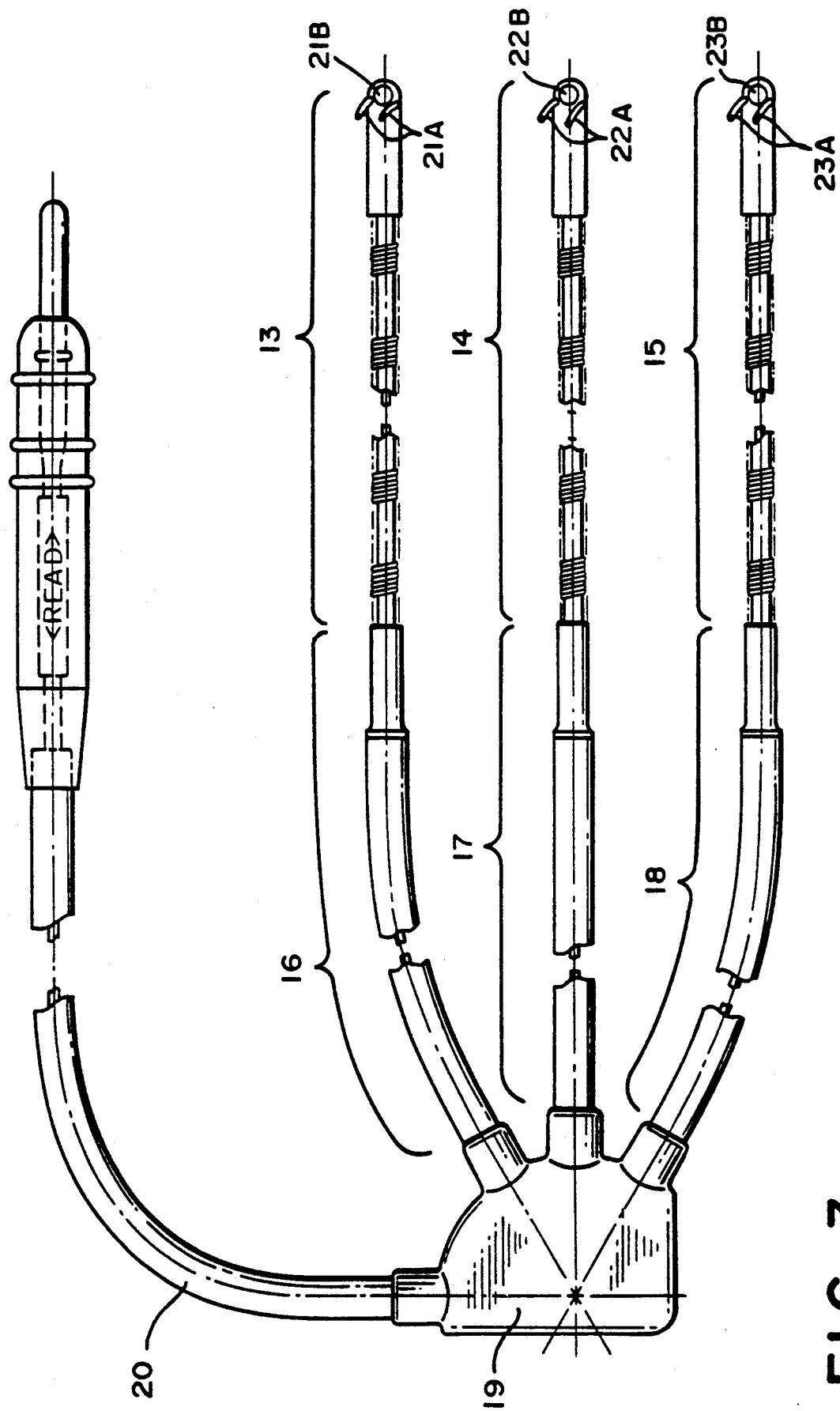

INSERTION AND TUNNELING TOOL FOR A SUBCUTANEOUS WIRE PATCH ELECTRODE

FIELD OF THE INVENTION

The present invention is related to the art of implantable defibrillating/cardioverting devices, and in particular, is related to a subcutaneous defibrillation electrode and an insertion and tunneling tool for implanting subcutaneous electrode segments through a minimal number of incisions.

BACKGROUND OF THE INVENTION

It is well known that cardiac arrhythmias, such as atrial or ventricular fibrillation, can be overcome by applying electrical energy to the arrhythmic myocardium. This procedure, commonly referred to as defibrillation or cardioversion, can be accomplished by applying the electrical energy either to the chest of the patient by means of conductive-metal paddles held in place by medical personnel or, during the course of cardiac surgery, by holding conductive-metal paddles in direct contact with the surface of the heart. Such procedures are well known and have been found to be generally effective in practice.

In addition, automatic defibrillation/cardioversion has been achieved by implanting an automatic defibrillating/ cardioverting device capable of detecting one of the aforementioned arrhythmias, and defibrillating/cardioverting the heart accordingly. Automatic defibrillating/cardioverting devices of this type have traditionally employed endocardial electrodes or epicardial electrodes, the latter of which is inserted in a rather invasive manner.

Additionally, another type of implantable electrode is a subcutaneous planar electrode, which does not violate the pleural cavity, and requires only minor surgery. A subcutaneous electrode is used in implantable cardioversion/defibrillation to discharge against one or more epicardial or endocardial electrodes. Subcutaneous electrodes heretofore known comprise a planar conductive screen. The implantation procedures for such subcutaneous electrodes require the formation of a subcutaneous pocket by blunt dissection, and the subsequent insertion of a suitable planar electrode. These planar subcutaneous electrodes result in discomfort in some patients, though they are used on a widespread basis in internal defibrillation/cardioversion.

The present invention relates to a tool and a method for implanting an array type or multi-segment subcutaneous electrode which is the subject of U.S. patent application Ser. No. 07/533,886, field Jun. 6, 1990. This type of subcutaneous electrode is as effective as planar electrodes and more comfortable than such planar electrodes. The present invention also relates to an improvement of the subcutaneous electrode disclosed in the aforementioned prior application.

SUMMARY OF THE INVENTION

It is a primary object of the present invention to overcome the aforementioned problems, by providing a tunneling tool for inserting a multi-segment subcutaneous electrode by way of a less traumatic procedure.

It is another object of the present invention, to provide a tunneling tool capable of inserting subcutaneous electrode segments through a minimal number of incisions.

It is a still further object of the present invention to accommodate the varying needs of many patients by providing a tunneling tool capable of accurately inserting subcutaneous electrode segments of various lengths.

It is a still further object of the present invention to provide a tunneling tool capable of reducing the surgical time required for inserting subcutaneous electrode segments.

In accordance with a first aspect of the present invention, a tunneling tool capable of implanting subcutaneous electrode segments in a patient, is provided, the tunneling tool being capable of implanting a plurality of electrode segments through a single incision. Hence, there is no need for a second incision unless suturing of the electrode segments to the body of the patient is desired. Similarly, because the electrode segments are of the subcutaneous type, there is also no need for highly invasive thoracic surgery.

To achieve its objectives, the tunneling tool of the present invention, comprises a stylet, an orientation spring, and a peel-away sheath having two pull tabs and a perforation. The orientation spring provides a means by which various electrode segment lengths can be accommodated, and in addition, provides an orientation reference to insure that the pull tabs of the sheath are oriented in a predetermined position with respect to the patient and the stylet. As an even further feature of the present invention, the tunneling tool can be constructed in a curved configuration to accommodate electrode implantation in the lateral subcutaneous region of the thorax.

During an implantation procedure and prior to being inserted into the patient, the stylet is inserted into the peel-away sheath, much in the same way that a conventional IV needle is inserted into an IV catheter. An incision is then made into the patient, preferably at the point where a yoke assembly combines the various electrode segment leads into one main lead body of the multi-segment lead, and the tunneling tool (stylet with sheath) is subsequently inserted through the incision and into the fat layer of the patient. After the tool is inserted into the patient to create a subcutaneous tunnel in a desired location, the stylet is removed from within the sheath, thereby revealing the resulting tunnel defined by the sheath, inside the patient. The aforementioned procedure is then repeated once for each electrode segment and its corresponding destination. With all of the sheaths appropriately positioned and the stylet removed, each of the individual electrode segments is inserted into its corresponding tunnel, and the peel-away sheaths are then removed by pulling on the two designated pull tabs.

As an alternative, the electrode segments can be implanted, and the corresponding sheaths removed, one by one. That is, each electrode segment can be implanted and its associated sheath withdrawn, before the insertion of another sheath or electrode segment.

Regardless of which technique is used, a plurality of electrode segments can be implanted subcutaneously in a patient without the need for extensive thoracic surgery, and usually, without the need for more than one incision. Subsequent incisions are only required when suturing of the distal ends of the electrode segments to the patient is desired. Also, as compared to conventional techniques, the tunneling tool of the present invention and the associated surgical procedure have been found to reduce the surgical time and trauma needed to implant subcutaneous electrodes by one-third.

In accordance with a second aspect, the present invention relates to a multi-segment subcutaneous defibrillation electrode having suture holes at the end of each segment and/or tines along the length of each segment for securing the segments to tissue in the patient.

The aforementioned and other objects, features, and advantages of the present invention will become subsequently apparent from the following description of the preferred embodiment, as well as from the associated drawings, all of which merely illustrate the inventive concept, and are in no way intended, nor should they be construed, to limit the scope of the instant invention.

BRIEF DESCRIPTION OF THE DRAWINGS

FIG. 3 illustrates an electrode and lead configuration for use in conjunction with the tunneling tool of the present invention.

DETAILED DESCRIPTION OF A PREFERRED EMBODIMENT

Figure 1:
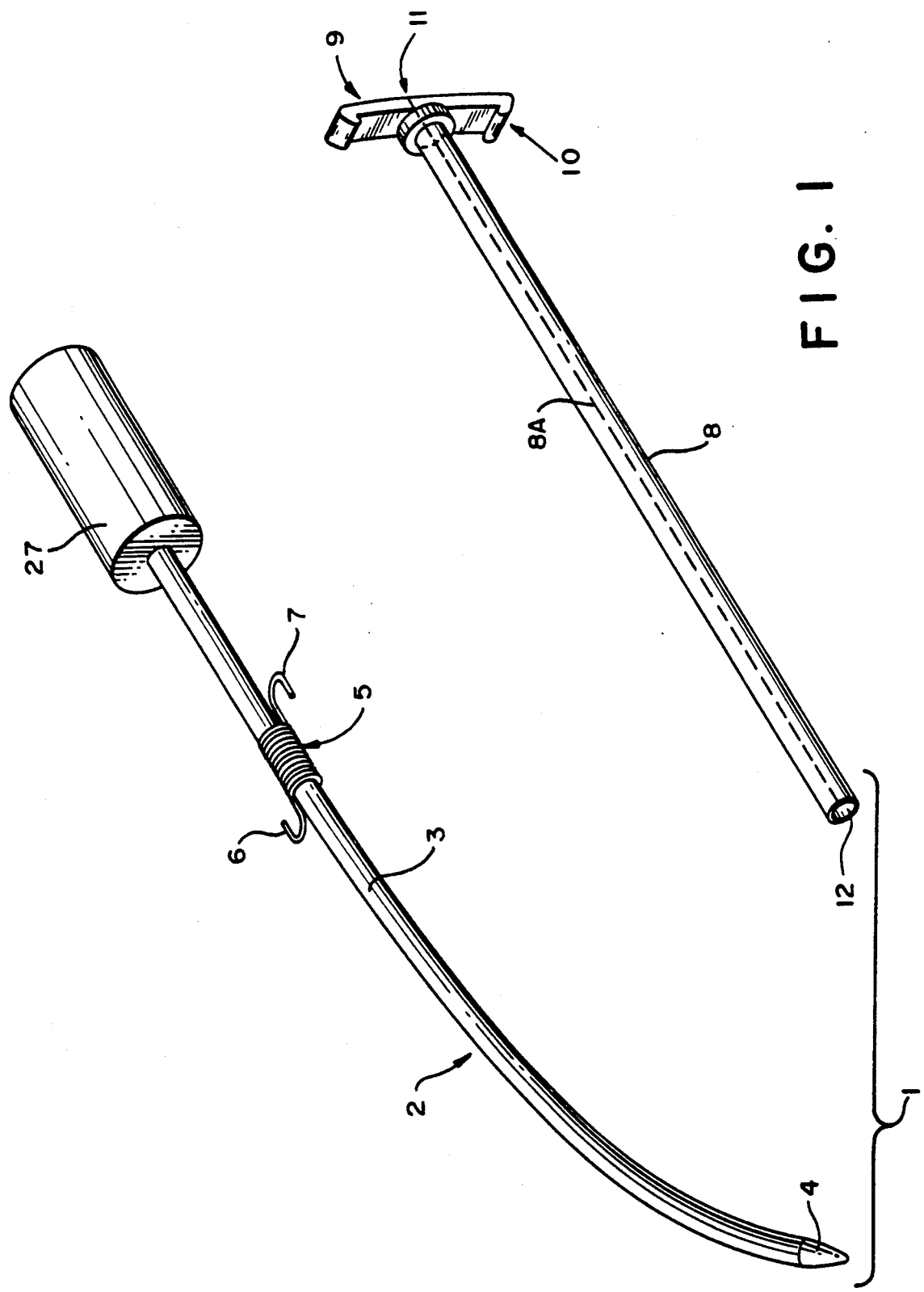
FIG. 1 illustrates a tunneling tool having a peel-away sheath and a stylet in accordance with the present invention.

A tunneling tool 1, in accordance with the present invention, is illustrated in FIG. 1, and comprises an elongated stylet 2 having a rigid body 3 and a slightly pointed distal tip 4; an orientation spring 5 having a catch hook 6 and a squeeze tab 7; and an elongated peel-away sheath 8 having two pull tabs 9 and 10, two openings 11 and 12, each opening 11 and 12 being located at opposite ends of the peel-away sheath 8, and a longitudinal perforation 8A orthogonally off set from the pull tabs 9 and 10. In general, the stylet 2 is constructed of rigid material such as stainless steel or surgical grade steel, while the peel-away sheath 8 is comprised of a more flexible material such as Teflon.

Figure 2:
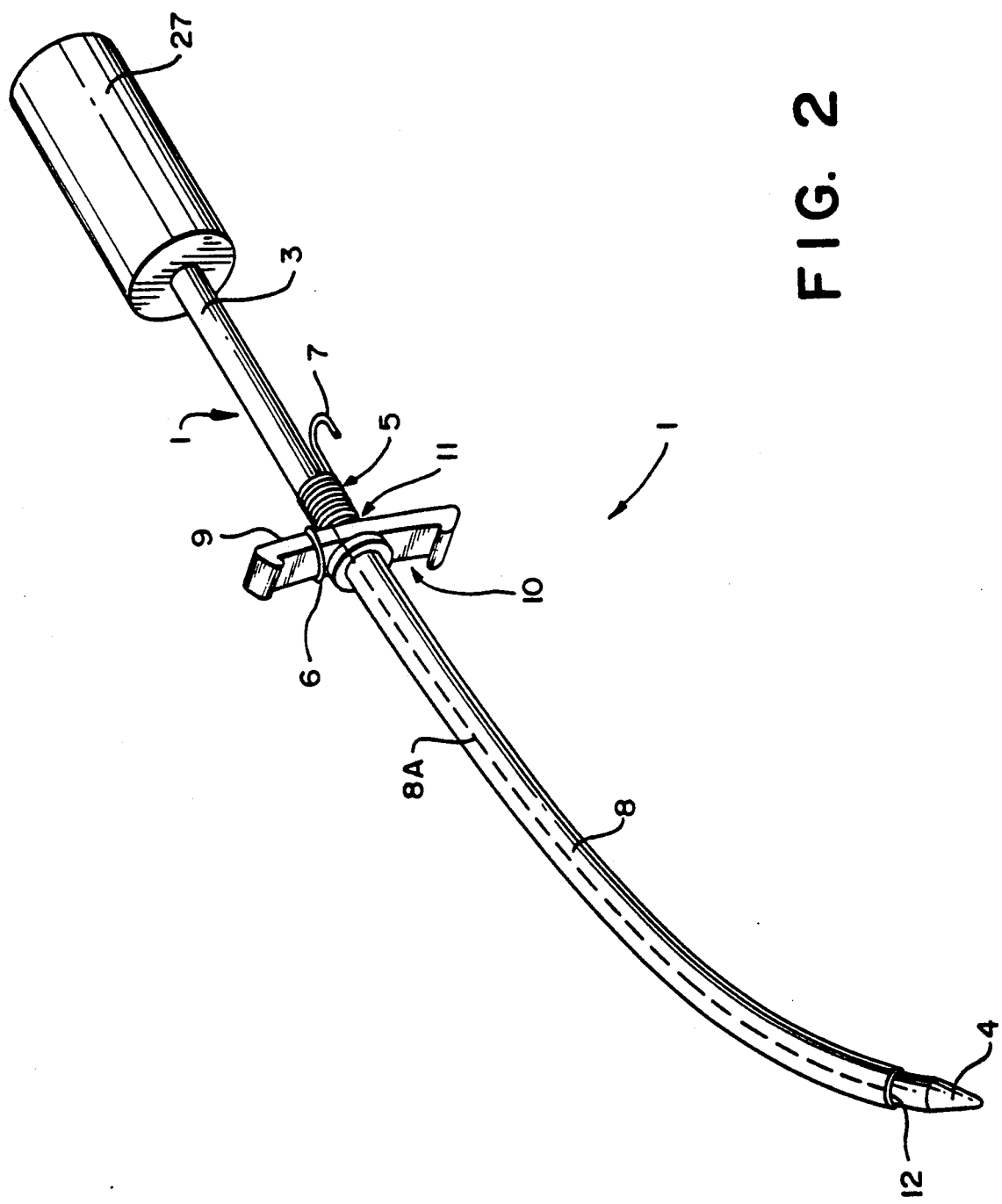
FIG. 2 illustrates the tunneling tool with the peel-away sheath mounted on the stylet.

With reference to FIG. 2, the distal tip 4 of the tunneling tool 1, is inserted into the opening 11 at a proximal end of the peel-away sheath 8, the proximal end corresponding to an end of the peel-away sheath 8 where the pull tabs 9 and 10 are located. The distal tip 4 of the stylet 2 is inserted into the peel-away sheath 8 until the distal tip 4 protrudes through the opening 12 at a distal end of the peel-away sheath 8. Ideally, the distal tip 4 should protrude one half inch beyond the opening 12.

Once the peel-away sheath 8 is properly positioned around the stylet 2 with the distal tip 4 appropriately protruding through the opening 12, the orientation spring 5 is adjusted so as to prevent any further relative motion between the stylet 2 and the peel-away sheath 8, and so as to maintain a parallel relationship between the pull tabs 9 and 10 and the body of the patient.

In particular, the orientation spring 5, is wrapped around the rigid body 3 of the stylet 2 under sufficient tension to apply a frictional force against the stylet 2 and thereby prevent spring 5 motion and rotation relative to the stylet 2. The spring 5 becomes positionally and rotationally adjustable by being twisted tangentially so as to increase the spring's cross sectional radius, and thereby reduce the frictional force that otherwise prevents the spring 5 from moving or rotating relative to the stylet 2. With the frictional force reduced, the orientation spring 5 is free to move into a longitudinal position corresponding to a selectively chosen peel-away sheath 8 length, an electrode segment size, and so as to maintain the aforementioned half inch relationship between the distal tip 4 of the stylet 2 and the opening 12 of the peel-away sheath 8.

In addition, the orientation spring 5 is also aligned tangentially to facilitate the use of the catch hook 6 to orient the pull tabs 9 and 10 toward a predetermined relationship with respect to the stylet 2, and to prevent further rotation between the stylet 2 and the pull tabs 9 and 10 after the predetermined relationship is achieved, the predetermined relationship usually causing the pull tabs 9 and 10 to be arranged parallel to the patient's body. Once the orientation spring 5 is properly positioned, the orientation spring 5 is decompressed so as to tighten around the stylet 2 at the appropriate position, and thereby prevent any further relative motion or rotation between the stylet 2 and the peel-away sheath 8.

In FIG. 2, it can be seen that the peel-away sheath 8 is constructed of a flexible material, and therefore, assumes the shape of the rigid body 3. It can also be seen that the rigid body 3 is designed with a curved configuration. This curved configuration facilitates tunneling in the lateral thoracic region of the human body.

The tunneling tool 1 of the present invention, has particularly useful applications related to the implantation of electrode segments for subcutaneous wire patch electrodes in lateral positions. An example of a wire patch electrode which is suitable for use in conjunction with the aforementioned tunneling tool 1, is the configuration illustrated in FIG. 3. FIG. 3 also illustrates the second aspect of the present invention relating to the improvement of the subcutaneous defibrillation electrode. Three electrode segments 13, 14, and 15 are connected to their corresponding segment leads 16, 17, and 18, respectively. All three segment leads 16, 17, and 18 are then combined at a yoke 19 into a main lead body 20, the main lead body 20 providing a link to the defibrillating/cardioverting circuit itself. In addition, a set of tines 21A, 22A, and 23A and suture holes 21B, 22B, and 23B are located at the distal ends of electrode segments 13, 14, and 15, respectively, for providing a means of fixing the electrode segments 13, 14, and 15 inside the patient after insertion by the tunneling tool 1 of the present invention. Additional tines (not illustrated) can also be positioned along the length of the each electrode segment 13, 14, and 15 for providing an added fixation means. The tines 21A-23A are angled back toward the proximal end of the segments to lodge into the tissue to secure the segments thereto. Additionally, the electrode segments may be sutured at the suture holes 21B-23B.

A subcutaneous wire patch electrode of the type illustrated in FIG. 3, is disclosed in commonly assigned U.S. patent application Ser. No. 07/533,886 filed Jun. 6, 1990. The tunneling tool 1 and the associated procedure for implanting such a wire patch electrode, provides the basis for the present invention.

Figure 4:
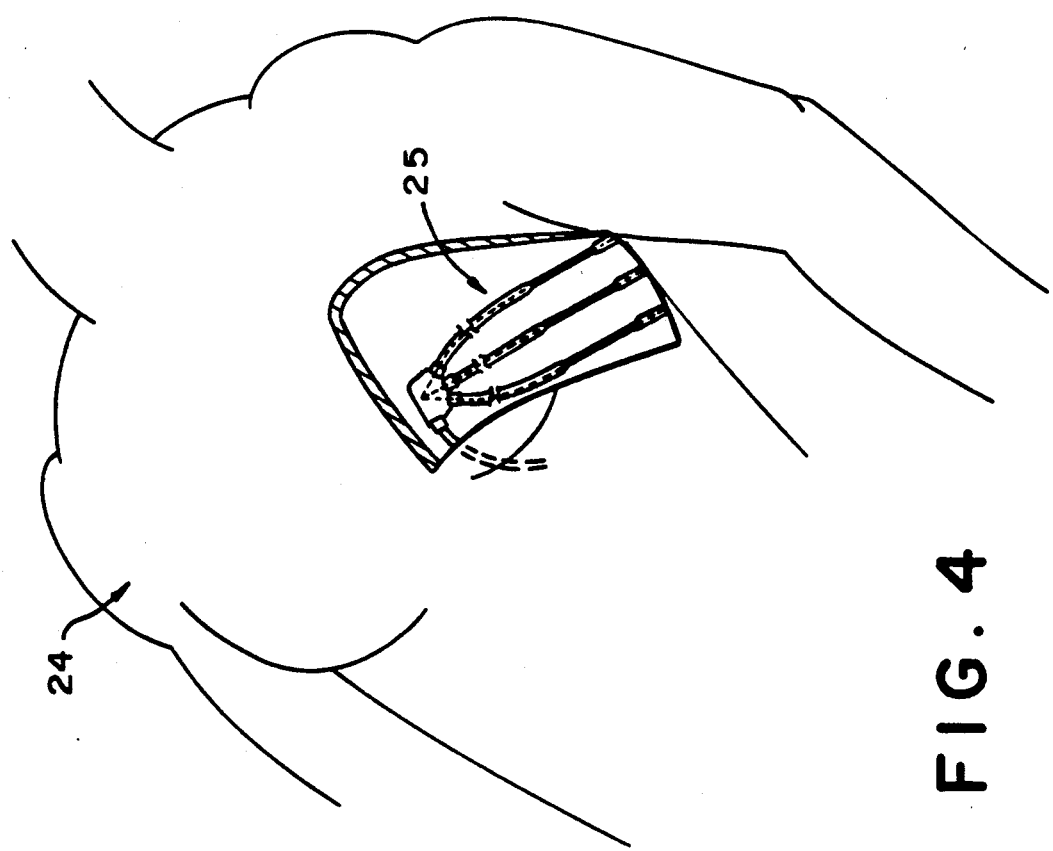
FIG. 4 illustrates the placement of one particular wire patch electrode.

Before implanting a subcutaneous wire patch electrode and its associated components, a physician must determine the type of lead configuration to be used and the desired electrode placement, as well as the size electrode segments to be used. As an example of one such electrode placement, FIG. 4 illustrates a patient 24 with a wire patch electrode 25 implanted in the lateral thoracic region. After such placement of an electrode has been decided upon by the physician, the tunneling tool 1 of the present invention is used to provide openings into which each electrode segment 13, 14, and 15 is placed.

Prior to implantation of the wire patch electrode 25, the orientation spring 5 is adjusted to accommodate a selectively chosen peel-away sheath 8 length corresponding to a particular electrode segment 13, 14, or 15 size. Proper adjustment of the spring 5 causes the distal tip 4 of the stylet 2 to protrude one half inch beyond the opening 12 in the peel-away sheath 8. The spring 5 is also adjusted so as to maintain a predetermined orientation between the pull tabs 9 and 10 and the curvature of the stylet 2, the orientation usually providing a parallel relationship between the pull tabs 9 and 10 and the body of the patient during an implantation procedure.

Figure 5:
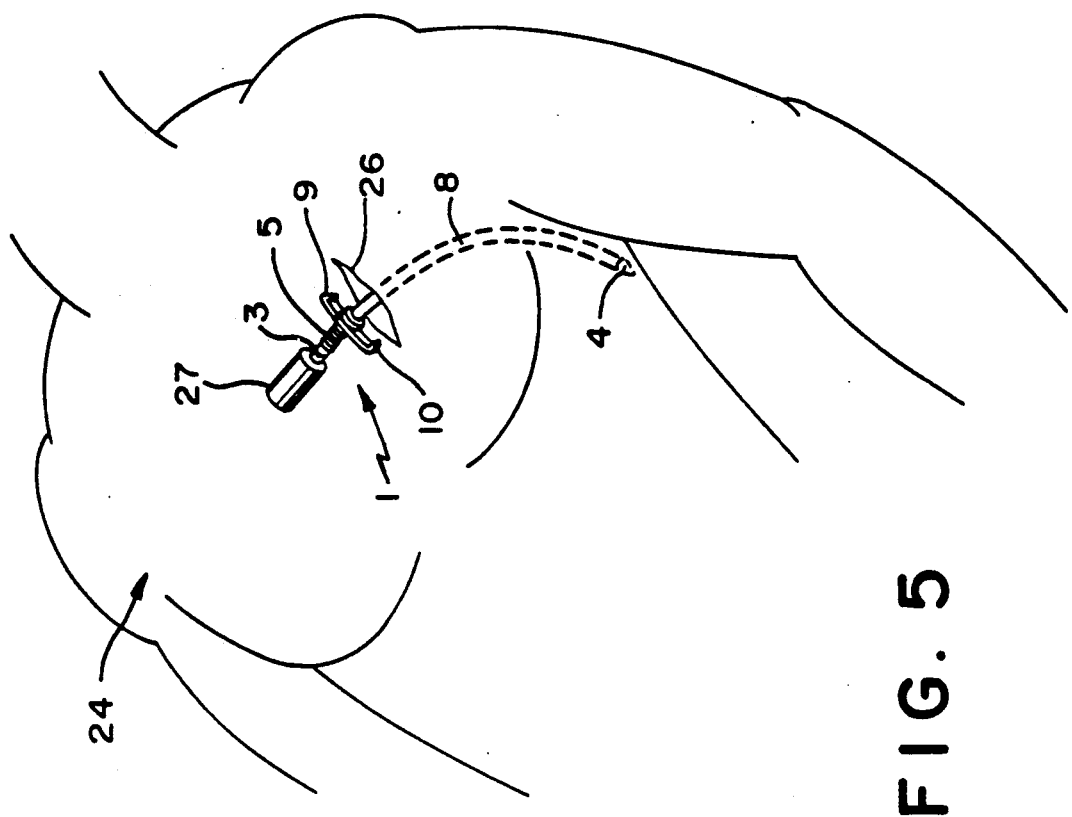
FIGS. 5-7 illustrate the steps of implanting an electrode segment with the tunneling tool of the present invention.

With reference to FIG. 5, after the stylet 2 has been appropriately inserted into the peel-away sheath 8, and the orientation spring 5 has been adjusted accordingly, an incision 26 is made into the patient 24 at a point where the yoke 19 is to be implanted. The incision 26 provides an opening into which the tunneling tool 1 is inserted subcutaneously into the fat layer of the patient 24, and in the direction of a desired tunnel. As the tunneling tool 1 is inserted, the distal tip 4 of the tunneling tool 1, makes its way through tissue, thereby creating the desired subcutaneous tunnel.

Figure 7:
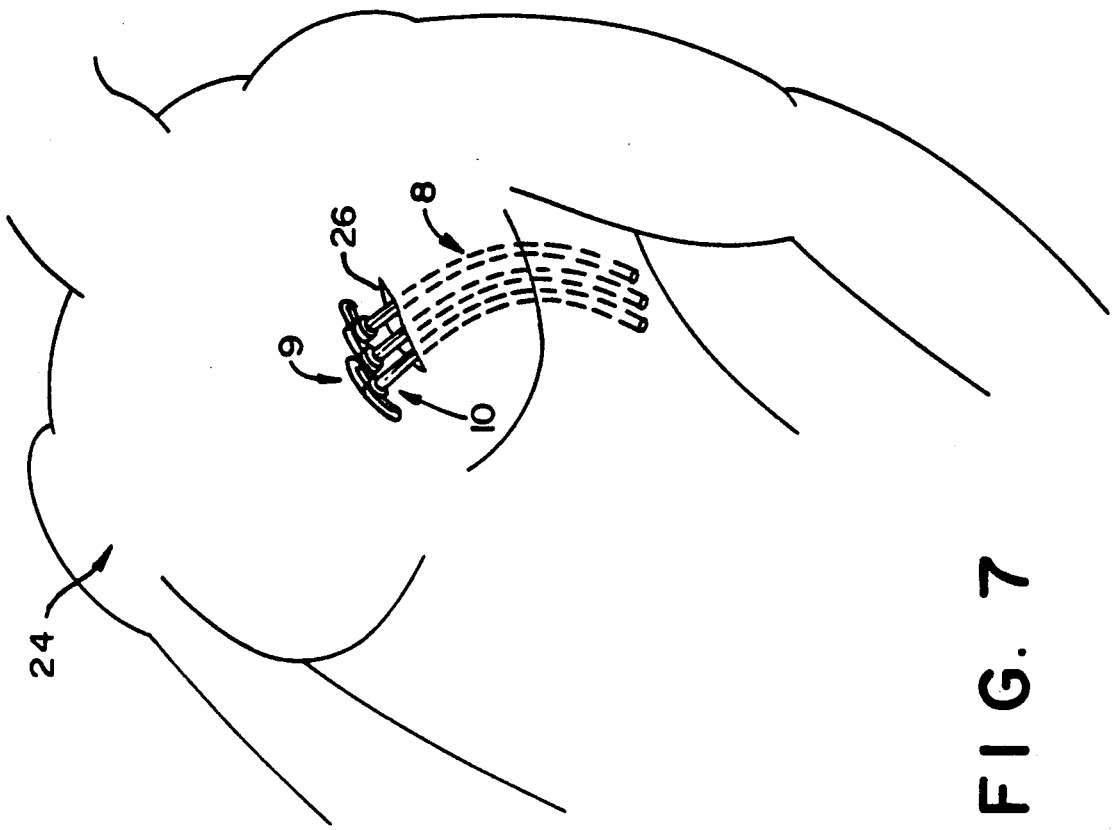
Figure 6:
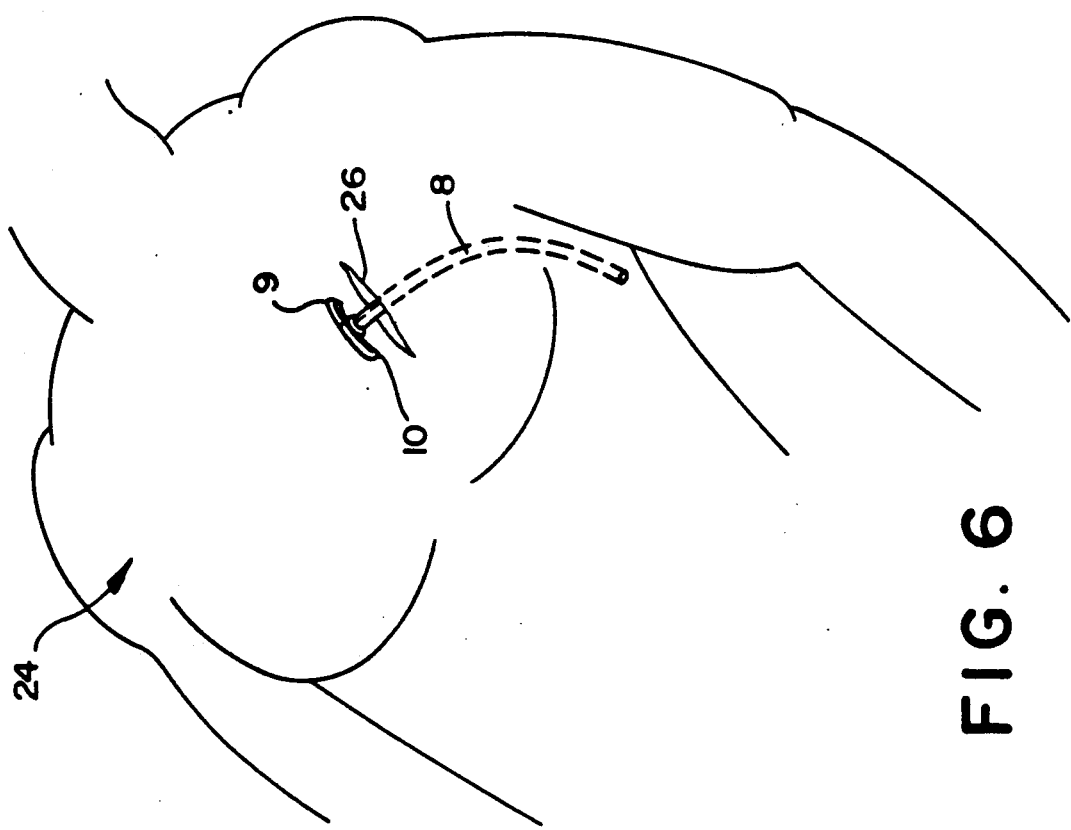

As illustrated in FIG. 6, once the peel-away sheath 8 and the stylet 2 are appropriately positioned in the patient's body, the stylet 2 is removed and the resulting tunnel formed by the peel-away sheath 8 is revealed. The aforementioned procedure is then repeated once, using the same incision 26, for every electrode segment which is to be implanted. The result, in the case of a three segment configuration, is illustrated in FIG. 7.

As soon as each tunnel is formed, each electrode segment 13, 14, and 15 of appropriate length, is inserted into its corresponding tunnel. The electrode segments 13, 14, and 15 are then attached to the body of the patient 24 by way of tines 21A, 22A, and 23A, respectively, which are mounted at the distal ends of each electrode segment 13, 14, and 15, and grab the surrounding tissue to prevent electrode migration. As an alternative to using only one incision, a second incision can be created through which the electrode segments 13, 14, and 15 can be sutured to the patient using the suture holes 21B, 22B, and 23B and conventional suturing techniques. As an even further alternative, the second incision can be replaced by a number of smaller incisions, each smaller incision corresponding to a particular suture hole 21B, 22B, or 23B, and each smaller incision providing an opening through which the electrode segments 13, 14, and 15 are sutured to the patient using conventional suturing techniques.

Figure 8:
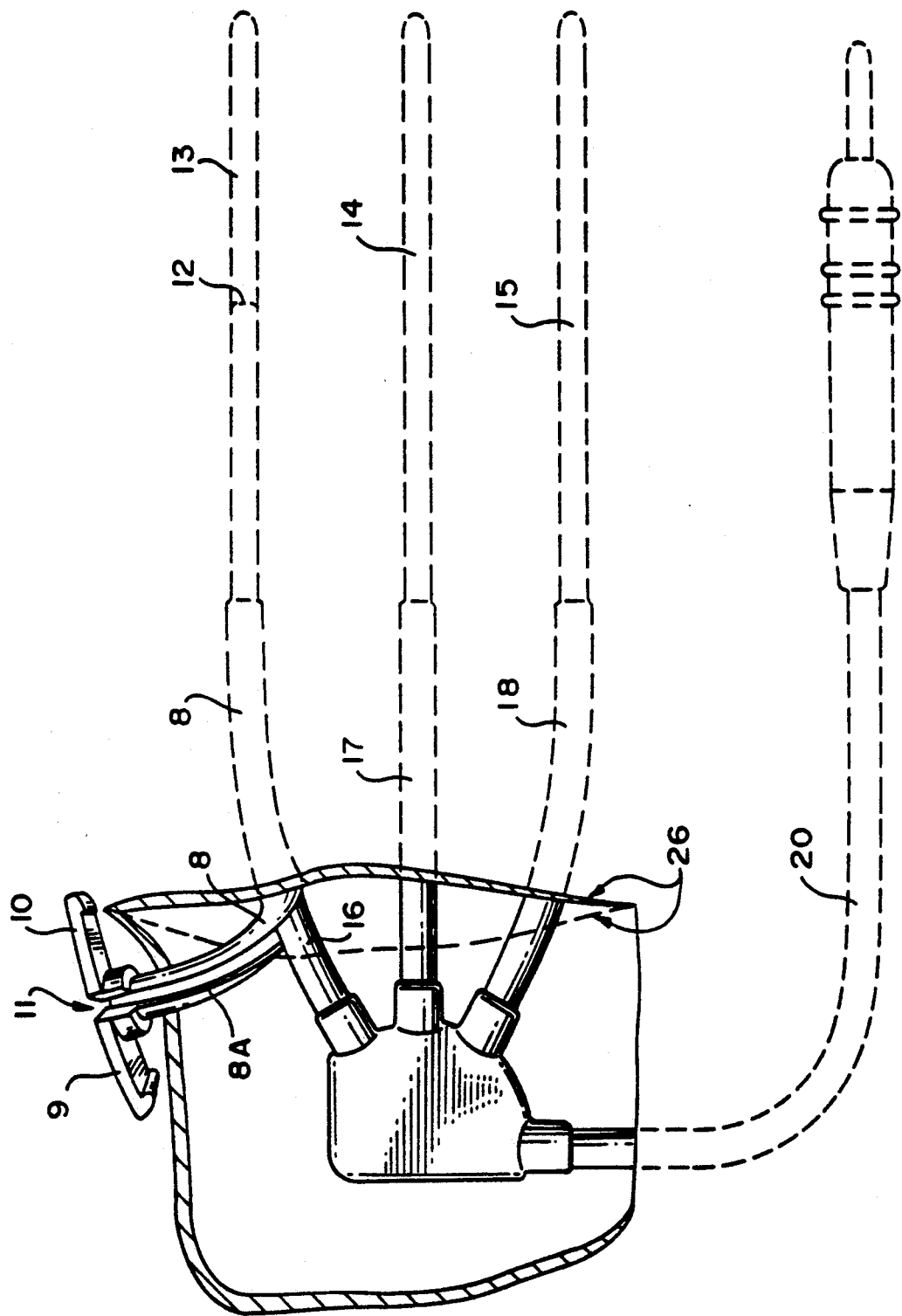
FIG. 8 illustrates the step of withdrawing the peel-away sheath in accordance with the present invention.

As illustrated in FIG. 8, once each electrode segment 13, 14, and 15 has been appropriately positioned in its proper location, or sutured as the case may be, the corresponding peel-away sheath 8 is removed by first pulling on the pull tabs 9 and 10 so as to split the longitudinal perforation 8A, and then withdrawing the peel-away sheath 8 from the patient. Splitting of the perforation 8A continues at the incision 26 until the peel-away sheath 8 is completely extracted from the patient and from the electrode lead 16, 17, or 18. Incidentally, although FIG. 8, for purposes of illustrating the perforation 8a, shows the peel-away sheath 8 bent during withdrawal, it is well understood that such bending does not actually occur. Instead, the peel-away sheath 8 is withdrawn in a virtually erect manner so that the pull tabs 9 and 10 maintain their parallel orientation with respect to the surface of the patient.

Furthermore, by having the tines 21A, 22A, and 23A angled back toward the incision 26 to thereby adhere to surrounding tissue, mere withdrawal of a peel-way sheath 8 is not sufficient to cause an inadvertent withdrawal of an electrode segment 13, 14, or 15. Similarly, the use of suturing techniques as mentioned above also prevents the inadvertent withdrawal of an implanted electrode segment 13, 14, and 15 during sheath 8 withdrawal.

As an added feature of the present invention the peel-away sheath 8 can also be constructed of radiopaque material so that fluoroscopic techniques can be used to verify peel-away sheath 8 positioning prior to electrode segment implantation. Accordingly, the peel-away sheath 8 can be repositioned upon detection of an inappropriate sheath 8 positioning.

In addition, the stylet 2 and the sheath 8 can also be designed with a larger diameter so that implantation of the main lead body 20 with a pulse generator, becomes possible. Also, because electrode segments of variable dimensions are needed to accommodate the varying needs of many patients, a plurality of peel-away sheath 8 lengths can be stocked, and can all be used on the same stylet 2 by simply adjusting the orientation spring 5 accordingly.

With reference to FIGS. 1, 2, and 3, the tunneling tool 1 can be equipped with a handle 27 to assist in maneuvering the tool 1 into a patient. Furthermore, because it is envisioned that electrode segments can be cut and sized by a physician to accommodate the individual needs of a particular patient, it may become necessary to crimp the sharp edges of the electrode segments with a crimping tube and a crimping mechanism to thereby avoid the high current gradients associated with the commonly known ledge effects of an electrode. Accordingly, the tunneling tool 1 can be equipped with a crimping mechanism, possibly incorporated in the handle 27 of the tunneling tool 1, for crimping the sharp edges of each electrode segment. To perform such a crimping operation, the crimp tube is placed over the end of an electrode segment, and is subsequently crimped onto the electrode segment by the crimping mechanism.

The foregoing is considered as illustrative only of the principles of the invention, and since numerous modifications and changes will readily occur to those skilled in the art, it is not desired to limit the invention to the exact construction and operation shown and described, and accordingly, all suitable modifications and equivalents may be resorted to, falling within the scope of the present invention.

We claim:
1. A tunneling tool for subcutaneously implanting electrode segments, said tunneling tool comprising:
at least one peel-away sheath for providing a subcutaneous tunnel into which an electrode segment is inserted for purposes of implantation in a patient, said peel-away sheath being removable after electrode segment implantation;

a stylet for inserting said at least one peel-away sheath subcutaneously into a patient, said stylet fitting snugly within said at least one peel-away sheath, and comprising a slightly pointed distal tip for tunneling through tissue, and a rigid body for providing structural support while the tunneling tool is inserted through said tissue; and means for maintaining a predetermined rotational orientation of said peel-away sheath with respect to the stylet and the patient.

2. The tunneling tool of claim 1, wherein said at least one peel-away sheath is provided with at least one pull tab for facilitating withdrawal from the patient by peeling off said at least one peel-away sheath after implantation of the electrode segments, and wherein the means for maintaining a predetermined rotational orientation is adapted for maintaining said at least one pull tab in a predetermined rotational orientation with respect to the stylet and the patient.

3. The tunneling tool of claim 1 further comprising an adjusting means for selectively maintaining a predetermined longitudinal orientation between the stylet and said at least one peel-away sheath.

4. The tunneling tool of claim 3, wherein the adjusting means comprises an adjustable orientation spring which is wrapped around the rigid body of the stylet, said spring being under sufficient tension to apply a frictional force against the stylet and thereby prevent spring motion relative to the stylet, said spring becoming positionally adjustable by being twisted tangentially so as to increase the spring's cross sectional radius, and thereby reduce the frictional force that otherwise prevents spring motion relative to the stylet.

5. The tunneling tool of claim 3, wherein the adjusting means also selectively maintains a predetermined rotational orientation between the stylet and said at least one peel-away sheath.

6. The tunneling tool of claim 5, wherein the adjusting means comprises an adjustable orientation spring which is wrapped around the rigid body of the stylet, said spring being under sufficient tension to apply a frictional force against the stylet and thereby prevent spring motion and rotation relative to the stylet, said spring becoming positionally and rotationally adjustable by being twisted tangentially so as to increase the spring's cross sectional radius, and thereby reduce the frictional force that otherwise prevents spring motion and rotation relative to the stylet.

7. The tunneling tool of claim 6, wherein said at least one peel-away sheath is provided with at least one pull tab for facilitating withdrawal from the patient by peeling off said at least one peel-away sheath after implantation of the electrode segments, and wherein the orientation spring is equipped with a catch hook for maintaining a predetermined orientation of said at least one pull tab with respect to the stylet and the patient.

8. The tunneling tool of claim 1, wherein said at least one peel-away sheath is provided with at least one pull tab for facilitating withdrawal from the patient by peeling off said at least one peel-away sheath after implantation of the electrode segments.

9. The tunneling tool of claim 1, wherein the stylet and said at least one peel-away sheath are constructed with a sufficiently large diameter to permit implantation of a main lead body.

10. The tunneling tool of claim 1, wherein said at least one peel-away sheath is provided with a coextensively longitudinal perforation and pull tabs for splitting said at least one peel-away sheath, for facilitating a peel-away withdrawal of said at least one peel-away sheath from the patient.

11. A tunneling tool for subcutaneously implanting electrode segments, said tunneling tool comprising:

at least one peel-away sheath for providing a subcutaneous tunnel into which an electrode segment is inserted for purposes of implantation in a patient, said peel-away sheath being removable after electrode segment implantation;

a stylet for inserting said at least one peel-away sheath subcutaneously into a patient, said stylet fitting snugly within said at least one peel-away sheath, and comprising a slightly pointed distal tip for tunneling through tissue, and a rigid body for providing structural support while the tunneling tool is inserted through said tissue; and wherein the rigid body of the stylet is constructed in a curved configuration for facilitating electrode segment implantation in the lateral thoracic region of a patient.

12. A tunneling tool for subcutaneously implanting electrode segments, said tunneling tool comprising:

at least one peel-away sheath for providing a subcutaneous tunnel into which an electrode segment is inserted for purposes of implantation in a patient, said peel-away sheath being removable after electrode segment implantation;

a stylet for inserting said at least one peel-away sheath subcutaneously into a patient, said stylet fitting snugly within said at least one peel-away sheath, and comprising a slightly pointed distal tip for tunneling through tissue, and a rigid body for providing structural support while the tunneling tool is inserted through said tissue; and wherein said at least one peel-away sheath is constructed of radiopaque material so that the positioning of said at least one peel-away sheath can be verified by fluoroscopic techniques and repositioned if necessary, prior to electrode segment implantation.

13. A method of implanting a subcutaneous electrode segment, said method comprising the steps of:

making an incision at a location of implantation;

inserting a tunneling tool into the incision, said tunneling tool having a stylet contained in a peel-away sheath, said tunneling tool being inserted with an orientation corresponding to the desired placement of an electrode segment subcutaneously in a patient;

withdrawing said stylet from said sheath upon achieving a desired placement of said tool subcutaneously in the patient, said withdrawal revealing a subcutaneous tunnel defined by said peel-away sheath;

inserting an electrode segment into said peel-away sheath;

withdrawing the peel-away sheath from the patient leaving the electrode segment in its proper position; and verifying the position of said peel-away sheath using fluoroscopic techniques prior to said step of inserting an electrode segment.

14. The method of claim 13, and further comprising the step of repositioning of said peel-away sheath upon detecting an inappropriate position during said step of verifying.

15. A method of implanting an electrode comprising at least one subcutaneous electrode segment, said method comprising the steps of:

making an incision at a location of implantation;

inserting a tunneling tool into the incision, said tunneling tool having a stylet contained in a peel-away sheath, said tunneling tool being inserted with an orientation corresponding to the desired placement of an electrode segment subcutaneously in a patient;

withdrawing said stylet from said sheath upon achieving a desired placement of said tool subcutaneously in the patient, said withdrawal revealing a subcutaneous tunnel defined by said peel-away sheath;

inserting subsequent peel-away sheaths using the same stylet to reveal subsequent subcutaneous tunnels, each peel-away sheath corresponding to a particular electrode segment which is to be implanted;

inserting an electrode segment into each of said peel-away sheaths;

withdrawing each peel-away sheath from the patient leaving the electrode segments in their proper positions; and adjusting the stylet to accept a particular peel-away sheath length and to maintain a predetermined longitudinal relationship between said stylet and said peel-away sheath.

16. The method of claim 15, and further comprising the step of attaching each electrode segment to the surrounding tissue of an implantation site, prior to said step of withdrawing each peel-away sheath from the patient.

17. The method of claim 16, wherein the step of attaching each electrode segment, includes making at least one more incision and subsequently suturing said electrode segment to the surrounding tissue through said at least one more incision.

18. The method of claim 15, and further comprising the step of attaching each electrode segment by way of tines to the surrounding tissue of an implantation site, prior to said step of withdrawing each peel-away sheath from the patient.

19. A method of implanting an electrode comprising at least one subcutaneous electrode segment, said method comprising the steps of:

making an incision at a location of implantation;

inserting a tunneling tool into the incision, said tunneling tool having a stylet contained in a peel-away sheath, said tunneling tool being inserted with an orientation corresponding to the desired placement of an electrode segment subcutaneously in a patient;

withdrawing said stylet from said sheath upon achieving a desired placement of said tool subcutaneously in the patient, said withdrawal revealing a subcutaneous tunnel defined by said peel-away sheath;

inserting subsequent peel-away sheaths using the same stylet to reveal subsequent subcutaneous tunnels, each peel-away sheath corresponding to a particular electrode segment which is to be implanted;

inserting an electrode segment into each of said peel-away sheaths;

withdrawing each peel-away sheath from the patient leaving the electrode segments in their proper positions; and verifying the position of said peel-away sheath using fluoroscopic techniques prior to said step of inserting an electrode segment.

20. The method of claim 19, and further comprising the step of repositioning said peel-away sheath upon detecting an inappropriate position during said step of verifying.

21. A tunneling tool for implanting a subcutaneous electrode in a patient, said electrode comprising at least one electrode segment, said tunneling tool comprising:

an elongated stylet having proximal and distal ends, a handle at the proximal end, a slightly pointed tip at the distal end for inserting through an incision to create a subcutaneous tunnel through tissue;

an elongated sheath having proximal and distal open ends, and receiving said stylet in a coextensive manner so that the slightly pointed tip at the distal end of the stylet extends out of the distal end of the sheath, and the proximal end of the sheath not extending beyond proximal end of the stylet, said sheath providing a subcutaneous tunnel when the stylet is removed from the sheath while the sheath is inside the patient; and wherein the stylet is provided with an adjusting means for maintaining a predetermined rotational and longitudinal positional relationship between the stylet and the sheath.

22. The tunneling tool of claim 21, wherein the adjusting means comprises an adjustable orientation spring which is wrapped around the stylet, said spring being under sufficient tension to apply a frictional force against the stylet and thereby prevent spring motion and rotation relative to the stylet, said spring becoming positionally adjustable and rotatable by being twisted tangentially so as to increase the spring's cross sectional radius, and thereby reduce the frictional force that otherwise prevents spring motion and rotation relative to the stylet.

23. The tunneling tool of claim 22, wherein said sheath is provided with pull tabs for facilitating withdrawal from the patient by peeling off the sheath after implantation of the electrode segments, and wherein the orientation spring is equipped with a catch hook for maintaining a predetermined orientation between the pull tabs and the body of a patient.

24. The tunneling tool of claim 21, wherein said sheath is provided with pull tabs for facilitating withdrawal from the patient by peeling off the sheath after implantation of the electrode segments.

25. The tunneling tool of claim 21, wherein the stylet and sheath are constructed with a sufficiently large diameter to permit implantation of a main lead body.

26. A tunneling tool for implanting a subcutaneous electrode in a patient, said electrode comprising at least one electrode segment, said tunneling tool comprising:

an elongated stylet having proximal and distal ends, a handle at the proximal end, a slightly pointed tip at the distal end for inserting through an incision to create a subcutaneous tunnel through tissue;

an elongated sheath having proximal and distal open ends, and receiving said stylet in a coextensive manner so that the slightly pointed tip at the distal end of the stylet extends out of the distal end of the sheath, and the proximal end of the sheath not extending beyond proximal end of the stylet, said sheath providing a subcutaneous tunnel when the stylet is removed from the sheath while the sheath is inside the patient; and wherein the stylet is constructed in a curved configuration for facilitating electrode segment implantation in the lateral thoracic region of the patient.

27. A tunneling tool for implanting a subcutaneous electrode in a patient, said electrode comprising at least one electrode segment, said tunneling tool comprising:

an elongated stylet having proximal and distal ends, a handle at the proximal end, a slightly pointed tip at the distal end for inserting through an incision to create a subcutaneous tunnel through tissue;

an elongated sheath having proximal and distal open ends, and receiving said stylet in a coextensive manner so that the slightly pointed tip at the distal end of the stylet extends out of the distal end of the sheath, and the proximal end of the sheath not extending beyond proximal end of the stylet, said sheath providing a subcutaneous tunnel when the stylet is removed from the sheath while the sheath is inside the patient; and wherein said sheath is constructed of radiopaque material so that fluoroscopic techniques can be used to verify peel-away sheath positioning prior to electrode segment implantation.

28. A method of implanting a subcutaneous electrode segment, said method comprising the steps of:

making an incision at a location of implantation;

inserting a tunneling tool into the incision, said tunneling tool having a stylet contained in a radiopaque peel-away sheath, said tunneling tool being inserted with an orientation corresponding to the desired placement of an electrode segment subcutaneously in a patient;

withdrawing said stylet from said radiopaque peel-away sheath upon achieving a desired placement of said tool subcutaneously in the patient, said withdrawal revealing a subcutaneous tunnel defined by said radiopaque peel-away sheath;

verifying the position of said radiopaque peel-away sheath using fluoroscopic techniques;

repositioning said radiopaque peel-away sheath upon detecting an inappropriate position during said step of verifying;

inserting an electrode segment into said radiopaque peel-away sheath; and withdrawing the radiopaque peel-away sheath from the patient leaving the electrode segment in its proper position.

29. The method of claim 28, and further comprising the step of attaching the electrode segment by way of tines to the surrounding tissue of an implantation site, prior to said step of withdrawing the radiopaque peel-away sheath from the patient.

30. The method of claim 28, and further comprising the step of attaching the electrode segment to the surrounding tissue of an implantation site, prior to said step of withdrawing the radiopaque peel-away sheath from the patient.

31. The method of claim 30, wherein the step of attaching the electrode segment to surrounding tissue, includes making at least one more incision and subsequently suturing said electrode segment to the surrounding tissue through said at least one more incision.

* * * * *